(12) United States Patent
O'Lenick

(10) Patent No.: US 8,956,596 B1
(45) Date of Patent: Feb. 17, 2015

(54) POLYMERIC ESTERS

(71) Applicant: Thomas George O'Lenick, Dacula, GA (US)

(72) Inventor: Thomas George O'Lenick, Dacula, GA (US)

(73) Assignee: SurfaTech Corporation, Lawrenceville, GA (US)

( * ) Notice: Subject to any disclaimer, the term of this patent is extended or adjusted under 35 U.S.C. 154(b) by 206 days.

(21) Appl. No.: 13/986,023

(22) Filed: Mar. 25, 2013

(51) Int. Cl.
- *A61K 8/00* (2006.01)
- *A23D 9/00* (2006.01)
- *A61K 8/37* (2006.01)
- *A61Q 17/04* (2006.01)
- *C07C 57/26* (2006.01)

(52) U.S. Cl.
CPC . *A61K 8/37* (2013.01); *A61Q 17/04* (2013.01); *C07C 57/26* (2013.01)
USPC .............. 424/59; 554/223; 554/224; 554/229

(58) Field of Classification Search
USPC ......................................................... 424/59
See application file for complete search history.

(56) References Cited

U.S. PATENT DOCUMENTS

| 8,192,727 | B1 | 6/2012 | O'Lenick | |
| 8,465,730 | B1 * | 6/2013 | O'Lenick | 424/59 |

* cited by examiner

*Primary Examiner* — Sean Basquill
*Assistant Examiner* — Andrew S Rosenthal

(57) ABSTRACT

The present invention is drawn to a process for improving the efficiency of sunscreens using a series of polyesters based upon sorbeth ethoxylates esterified with fatty acids, then crosslinked with dimer acid. These polyesters exhibit a synergistic interaction with sunscreen actives improving the efficiency providing a "shield" for the body from the harmful effects of the sun. These sorbitol alkoxylates are then reacted with dimer acid, resulting in a series of novel polyesters. The linking of the two spider esters together with dimer provide an amphilic macromolecule possessing both hydrophilic and hydrophobic portions covalently bonded to the same molecule, this provides both a boost in sun protection factor (SPF) and the ability for the sunscreen actives to be applied to wet skin.

12 Claims, No Drawings

POLYMERIC ESTERS

RELATED APPLICATIONS

This application claims priority to and benefit of U.S. Provisional Application No. 61/741,670 filed Jul. 26, 2012, the disclosure of which is incorporated herein for all purposes.

BACKGROUND OF THE INVENTION

Due to the rise of melanoma and other skin related diseases, protection of the skin from the deleterious effects of the sun has become a priority in recent years. The quest for complete protection form the sun has lead to numerous research efforts of not only effective sun blockers but also products that are extremely efficient. A product that protects a wide variety of ultra violet (UV) radiation and is effective has become a priority. The effectiveness of sunscreen products are typically listed in terms of sun protection factor (SPF). The SPF can be altered by a variety of factors including the specific sunscreen agents chosen and the type of delivery systems (formula) chosen.

Sunscreen products work based on the ability of the sunscreen actives to absorb photons in the Ultraviolet B and Ultraviolet A range (UVB and UVA respectively). Simply put according to Beers Law Absorbance of light passing through a liquid is directly related to the concentration of absorbing material in the liquid. If one notes the published absorbance of sunscreen actives approved for use in the United States it can readily be deduced that many sunscreens utilized actives at levels many times greater than that should be necessary to obtain the desired SPF. This can be attributed to several factors but certainly one that is extremely important is the sunscreen active solvent system used in the formulations.

Sunscreens have been assigned Sun Protection Factor (SPF) values by the U.S. Food and Drug Administration (FDA) since 1978. SPF is a number that refers to the sunscreen product's ability to block UVB radiation. This number does not show the blockade against ultraviolet UVA radiation. Sunscreen products with SPFs of 2 to 50 are currently available. A sunscreen product with a SPF of 15 will protect your skin 15 times longer from UVB than if you did not have sunscreen applied. The exact amount of time will vary from person to person, the altitude, and proximity to the equator. SPF 15 will block 95% of the UVB wavelengths. SPF 30 does not work twice as well however, it will provide another 3% of protection.

Broad-spectrum sunscreens were developed to absorb both UVA and UVB energy. To achieve coverage over the UVA and UVB spectra, multiple sunscreens are selected both on the basis of absorbed wavelength range as well as other properties (i.e., water resistance, hypoallergenicity). A prevailing paradigm in sunscreen formulation has been "more is better". Many follow the approach that high SPF or more Boots stars can best be achieved by including many sunscreens in high concentrations. Because many sunscreens have decreased performance characteristics (e.g., lower SPF) when exposed to natural light, adherents of this school of formulation add more sunscreen actives than should theoretically be required to achieve a certain SPF. In so doing, they compensate for the degradation that takes place in the laboratory setting. However, this reasoning is flawed. There is markedly more photodegradation in natural sunlight, causing the actual SPF realized by the consumer to be lower.

The "more is better" paradigm also overlooks the fact that among the degradation products in photolabile sunscreens are free radicals, which can cause damage to DNA and other cellular molecules. Over time, free radical damage may become irreversible and lead to disease including cancer. Moreover, to the extent that a sunscreen is photolabile under artificial light (e.g., JCIA, COLIPA), that same composition could undergo more photodegradation, and produce more free radicals, when exposed to UVR as well as infrared and visible light under ambient conditions. Thus, a third objective of the present invention is to identify a combination sunscreen composition where after irradiation under ambient light each sunscreen active is photostable and thereby minimize the formation of potentially harmful free radicals.

Until recently, there have been three major types of sunscreen formulations: water in oil emulsion, the oil in water emulsion and the alcohol based formulation. All have their respective advantageous and disadvantageous. There have been formulation problems in making high SPF systems using oil-based sprays, including: application onto the skin and skin feel.

It has recently been discovered that the solvent effects can have a dramatic effect upon the SPF of a given formulation of sunscreen product. Solvent effects can be used to improve has a formulation's efficiency. By efficiency is meant the SPF that is obtained with a given level of sunscreen agent. The key to increasing the SPF of a formulation without altering the type of concentration of sunscreen is selecting the proper solvent.

A very useful and efficient tool for improving the SPF and absorption of a particular sunscreen is to modify the environment (i.e. the solvent) in which the active ingredients are placed. The modification of the environment can have a drastic effect on the over all performance of the sunscreen ranging from SPF, excitation wavelength, water tolerance and flammability of sunscreen.

Typically organic sunscreens absorb UV radiation by promoting electrons into an excited state. The effectiveness of the organic sunscreens are based on a couple of factors: the amount of energy (wavelength) that is required to promote an electron and how long the electron stays promoted before returning to the ground state. There are several ways that electrons can return to the ground state; they release the "stored" energy all at once and emit a different frequency of energy (fluoresces), they can transfer their energy to another molecule, or they can dissipate the energy as thermal heat. All three of these ways are directly related to the solvent the active ingredients are contained in.

Avobenzone, a common organic sunscreen, undergoes a keto/enol tautomerization. When avobenzone is placed into a polar environment, i.e. alcohol, the equilibrium lies heavily on the enol side. This results in a boost in SPF of the avobenzone. Solvent molecules can also transfer hydrogen atoms with excited molecules and "trap" them in a non-excitable state. This leaves the active sunscreen unable to promote an electron and therefore unable to absorb UV radiation. Beyer et al. used Raman spectroscopy to show that the excited state of N,N-dimethyl-p-amino-benzoic acid can accept a proton from a polar solvent resulting in loss of conjugation throughout the molecule. The interaction between active ingredients and the solvent can be easily modified and adjusted to fit the products needs.

An effective way of affecting the performance of organic sunscreens is to load them into delivery systems. Delivery systems most commonly involve amphiphilic systems, emulsions or amphiphilic macromolecules. Both emulsions and macromolecules act in the same manor. In oil in water emulsion, there are pockets of hydrophobic oil contained in the core of micelles. When hydrophobic organic sunscreens are added into the emulsion, they migrate into the hydrophobic micelle cores and remain suspended in a unified matrix. This organization provides two major advantages, firstly they pockets of actives provide a big boost in SPF and lastly the organization prevents aggregation of the organics, this removes color from the sunscreens on the skin. Macromolecules and polymers respond in the same way as emulsions, with the major difference being that the hydrophobic and hydrophilic portions of the formula are covalently attached to each other.

There has been a long felt need to provide formulations in which the SPF is increased providing longer protection with the same concentration of sunscreen. The new paradigm is less is more, that is less sunscreen actives formulated with the proper additives will provide significantly increases protection. The ability to so formulate products has been heretofore unattainable before the compounds of the present invention were developed.

FIELD OF THE INVENTION

The present invention is drawn to (a) novel polyester compounds and (b) a process for the use of the polyesters, which improves the efficiency of sunscreen actives. By efficiency is meant the increasing of the SPF (sun protection factor) in formulations containing the polyesters of the present invention (marketed under the trade name "SurfaShield™") compared with the same amount of sun screening actives in a formulation that do not contain the polyesters of the present invention. SurfaShield is a registered trademark of SurfaTech Corporation. These esters are derived from alkoxyated polyesters cross-linked with dimer acid. These polyesters exhibit a synergistic interaction with sunscreen actives, which improves the efficiency of the sunscreen, providing a "shield" for the body from the harmful effects of the sun. The amphilic nature of these polyesters provide a novel frame work capable of both enhancing a sunscreens SPF, while allowing the capability of the hydrophobic sunscreen actives to be applied uniformly on wet skin.

THE INVENTION

Object of the Invention

One object of the present invention is to provide a series of unique cross-linked polyesters that are amphilic in nature. Amphilic is a term used to describe a macromolecule that contains both a hydrophobic (water-hating) proton and a hydrophilic (water-loving) portion covalently bonded in the same molecule. The hydrophobic portion of the polyesters encapsulates the hydrophobic sunscreen actives. This encapsulation allows for hydrophobic materials to be introduced into a polar atmosphere without precipitation.

Another objective of the present invention is to provide a vehicle to improve water solubility of antioxidants, sunscreen actives and free radical scavengers to allow for through and efficient delivery of these materials to the skin in a more efficient way.

Other objections of the invention will become clear as the specifications and disclosures sections of this patent.

All temperatures specified herein are degrees C., all percentages are percentages by weight and all patents referred to herein are incorporated herein by reference.

SUMMARY OF THE INVENTION

The present invention relates to a process for improving the efficiency of sunscreens. The term efficiency is meant by a process of increasing a sunscreens sun protection factor (SPF) as well as providing the ability of hydrophobic sunscreen actives to the surface of "wet" skin. The process comprises of the encapsulation and transport of sunscreen actives by the use of a series of unique polyesters.

The polyesters of the present invention are cross-linked sorbeth ethoxylated fatty esters crosslinked through a dimer acid ester linkage group. The linkage with dimer acid forms a covalent bond between two different sorbeth ethoxylated fatty esters. This creates the possibility of covalently linking two different macromolecules with different physical properties to the same polymer backbone. The properties of the linked groups can be the molar ratio of fatty ester groups to hydroxyl groups. These materials are amphilic in nature. This provides many interesting properties including solubility in many different solvents, ability to encapsulate hydrophobic or hydrophilic materials, and the transport of the encapsulated materials into solvents that the materials are otherwise not soluble in. The process of using these compounds for improving the efficiency of sunscreens comprises the encapsulation of the sunscreen actives and transporting them to the skin with an effective concentration of the esters of the present invention.

DETAILED DESCRIPTION OF THE INVENTION

One aspect of the present invention is a series of esters having the following structure:

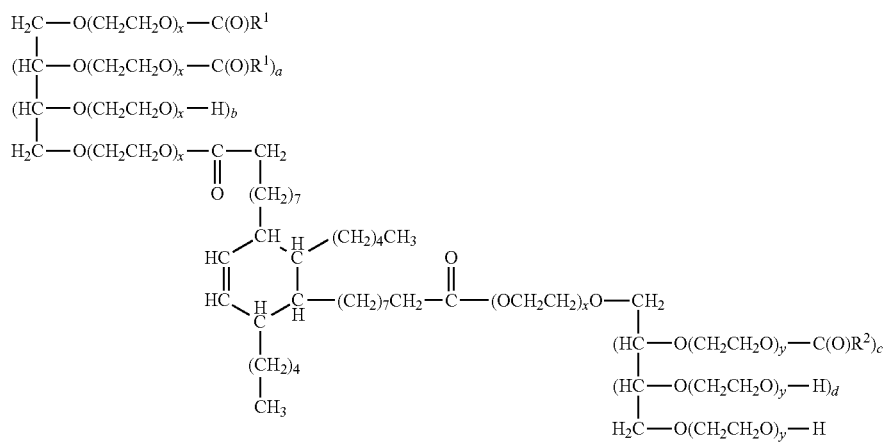

wherein;
$R^1$ is an alkyl having 7 to 21 carbons atoms;
$R^2$ is an alkyl having 7 to 21 carbons atoms;
x is an integer ranging from 1 to 10;
y is an integer ranging from 1 to 10;
a is an integer ranging from 0 to 4;
b is an integer ranging from 0 to 4, with the proviso that a+b equals 4;
c is an integer ranging from 0 to 4;
d is an integer ranging from 0 to 4, with the proviso that c+d equals 4.

Another aspect of the present invention is a series of esters prepared by the reaction of;
(a) and ethoxylated sorbeth esters conforming to the following structure:

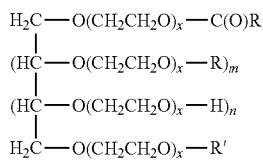

wherein;
R is an alkyl having 7 to 21 carbons atoms;
R' is an —C(O)—R;
x is an integer ranging from 1 to 10;
m is an integer ranging from 0 to 4;
n is an integer ranging from 1 to 4, with the proviso that m+n equals 4;
(b) a dimer acid compound selected from the group consisting of dimer acid and hydrogenated dimer acid.

Another aspect of the present invention is directed to a process for improving the efficiency of sunscreens which comprises contacting the skin with an effective protecting concentration of a composition comprising:

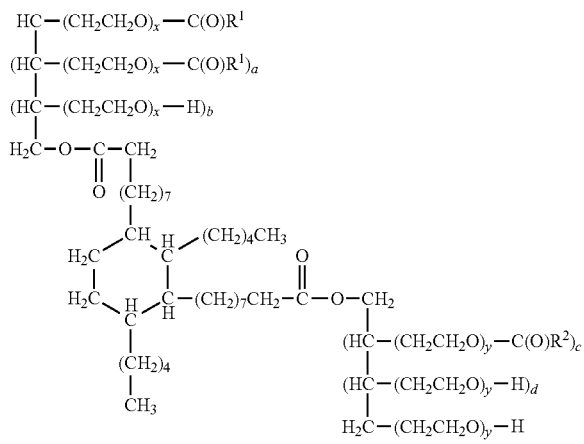

wherein;
$R^1$ is an alkyl having 7 to 21 carbons atoms;
$R^2$ is an alkyl having 7 to 21 carbons atoms;
x is an integer ranging from 0 to 10;
y is an integer ranging from 0 to 10;
a is an integer ranging from 0 to 4;
b is an integer ranging from 0 to 4, with the proviso that a+b equals 4;
c is an integer ranging from 0 to 4;
d is an integer ranging from 0 to 4, with the proviso that c+d equals 4.
and sunscreening actives.

A wide variety of conventional organic sunscreen actives are suitable for use herein. Sagarin, et al., at Chapter VIII, pages 189 et seq., of Cosmetics Science and Technology (1972), discloses numerous suitable actives. Specific suitable sunscreen actives include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pylneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl)ether; hydroquinone; benzophenones (oxybenzone, sulisobenzone, dioxybenzone, benzoresorcinol, 2,2',4,4'-tetrahydroxybenzophenone, 2,2'-dihydroxy-4, 4'-dimethoxybenzophenone, octabenzone; 4-isopropyldibenzoylmethane; butylmethoxydibenzoylmethane; etocrylene; octocrylene; [3-(4'-methylbenzylidene boman-2-one), terephthalylidene dicamphor sulfonic acid and 4-isopropyl-di-benzoylmethane.

Of these, 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-trimethylcyclohexylsalicylate, methylanthranilate, p-dimethylaminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and mixtures of these compounds, are preferred.

More preferred organic sunscreen actives useful in the compositions useful in the subject invention are 2-ethylhexyl-p-methoxycinnamate, butylmethoxydibenzoyl-methane, 2-hydroxy-4-methoxybenzo-phenone, 2-phenylbenzimidazole-5-sulfonic acid, octyldimethyl-p-aminobenzoicacid, octocrylene and mixtures thereof.

Also particularly useful in the compositions are sunscreen actives such as those disclosed in U.S. Pat. No. 4,937,370 issued to Sabatelli on Jun. 26, 1990, and U.S. Pat. No. 4,999, 186 issued to Sabatelli & Spirnak on Mar. 12, 1991. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy-4-(2-hydroxyethoxy) benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy) dibenzoylmethane and mixtures thereof.

Preferred Embodiments

In a preferred embodiment x is 1.
In a preferred embodiment x is 3.
In a preferred embodiment x is 5.
In a preferred embodiment x is 7.
In a preferred embodiment x is 10.

Examples

Sorbitol Alkoxylates

Sorbitol is 2,3,4,5,6-pentahydroxy hexanol. It has a CAS number of 50-70-4.

Sorbitol alkoxylates used in the present invention are commercially available from several sources including Siltech LLC, of Lawernceville, Ga. They are made by the addition of ethylene oxide to sorbitol. The conform to the following structure;

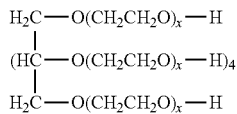

wherein;
x is an integer ranging from 1 to 10.

| Example | X | Molecular Weight (g/mol) |
|---|---|---|
| 1 | 1 | 446 |
| 2 | 3 | 976 |
| 3 | 5 | 1502 |
| 4 | 7 | 2030 |
| 5 | 10 | 2822 |

Fatty Acids

Fatty acids useful in the practice of the present invention are items of commerce they are available as either single components or mixtures.

Fatty acids useful as raw materials in the preparation of compounds of the present invention are commercially available from a variety of sources including Procter and Gamble of Cincinnati Ohio.

The structures are well known to those skilled in the art.

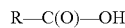

Saturated

| Example | R Formula | Common Name | Molecular Weight |
|---|---|---|---|
| 6 | $C_7H_5$ | Caprylic | 144 |
| 7 | $C_9H_{19}$ | Capric | 172 |
| 8 | $C_{11}H_{23}$ | Lauric | 200 |
| 9 | $C_{13}H_{27}$ | Myristic | 228 |
| 10 | $C_{14}H_{29}$ | Pentadecanoic | 242 |
| 11 | $C_{15}H_{31}$ | Palmitic | 256 |
| 12 | $C_{17}H_{35}$ | Stearic | 284 |
| 13 | $C_{19}H_{39}$ | Arachidinic | 312 |
| 14 | $C_{21}H_{43}$ | Behenic | 340 |
| 15 | $C_{26}H_{53}$ | cetrotic | 396 |
| 16 | $C_{33}H_{67}$ | geddic acid | 508 |

Unsaturated

| Example | R Formula | Common Name | Molecular Weight |
|---|---|---|---|
| 17 | $C_{17}H_{33}$ | Oleic | 282 |
| 18 | $C_{17}H_{31}$ | Linoleic | 280 |
| 19 | $C_{17}H_{29}$ | Linolenic | 278 |
| 20 | $C_{15}H_{29}$ | Palmitoleic | 254 |
| 21 | $C_{13}H_{25}$ | Myristicoleic | 226 |
| 22 | $C_{21}H_{41}$ | Erucic | 338 |

Sorbitol Alkoxylate Fatty Esters

Sorbitol alkoxylate fatty esters were prepared by SurfaTech Corporation, of Lawrenceville, Ga. They are prepared by the esterification of sorbitol alkoxylates (examples 1-5) with fatty acids (examples 6-22). They conform to the following structure;

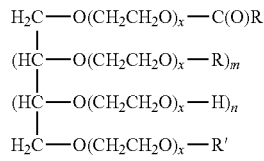

wherein;
R is an alkyl having 7 to 21 carbons atoms;
R' is an —C(O)—R;
x is an integer ranging from 1 to 10;
m is an integer ranging from 0 to 4;
n is an integer ranging from 1 to 4, with the proviso that m+n equals 4.

Examples

Esterification Reactions

In addition to the ratio of polyoxyalkylene groups to fatty groups and the linkage group chosen, it is very important for the practice of the current invention resulting in a compounds of the present, to have the correct ratio of hydroxyl groups to esterified polyoxyalkylene groups. The compounds of the present invention have a wide variety of unreacted hydroxyl groups.

General Procedure

A specified number of grams of the specified alkoxylate (Examples 1-5) is added to a specified amount of fatty acid (Examples 6-22). The reaction mixture is heated to 160-180° C. Water is removed by vacuum during the reaction process.

The reaction is monitored by determination of acid value. The acid value will diminish as the reaction proceeds. The reaction is cooled once the acid value fails to change over an additional two hours at temperature. The product is used without purification.

Sorbeth Pentaesters

These esters have on average five of the six ester groups esterified, leaving only one group left to react.

| | Sorbitol Ethoxylates | | Fatty Acid | |
|---|---|---|---|---|
| Example | Example | Grams | Example | Grams |
| 23 | 1 | 446 | 6 | 720 |
| 24 | 2 | 976 | 10 | 1210 |
| 25 | 3 | 1502 | 15 | 1980 |
| 26 | 4 | 2030 | 17 | 1410 |
| 27 | 5 | 2882 | 22 | 1690 |

Sorbeth Triesters

These esters have on average three of the six ester groups esterified, leaving on average three group left to react.

| | Sorbitol Ethoxylates | | Fatty Acid | |
|---|---|---|---|---|
| Example | Example | Grams | Example | Grams |
| 28 | 1 | 446 | 8 | 516 |
| 29 | 2 | 976 | 11 | 768 |
| 30 | 3 | 1502 | 19 | 834 |
| 31 | 4 | 2030 | 14 | 1020 |
| 32 | 5 | 2882 | 6 | 432 |

Sorbeth Monoesters

These esters have on average one of the six ester groups esterified, leaving on average five groups left to react.

| | Sorbitol Ethoxylates | | Fatty Acid | |
|---|---|---|---|---|
| Example | Example | Grams | Example | Grams |
| 33 | 1 | 446 | 6 | 144 |
| 34 | 2 | 976 | 17 | 282 |
| 35 | 3 | 1502 | 8 | 200 |
| 36 | 4 | 2030 | 14 | 340 |
| 37 | 5 | 2882 | 6 | 144 |

Example 38

Dimer Acid

Dimer acid is an item of commerce available commercially from Henkel Corporation. It conforms to the following structure:

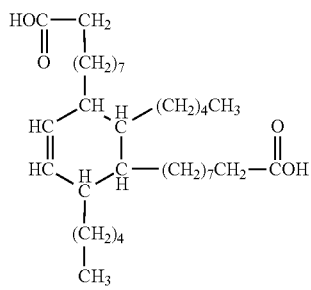

Example 39

Hydrogenated Dimer Acid

Hydrogenated dimer acid is an item of commerce available commercially from Henkel Corporation. It conforms to the following structure:

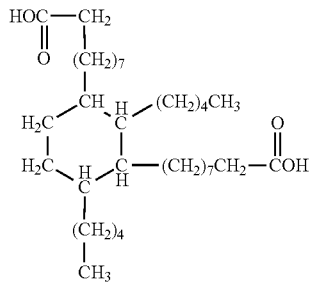

Reaction with Dimer Acid

A specified number of grams of the specified alkoxylate (Examples 23-37) is added to a specified amount of dimer acid (Example 38). The reaction mixture is heated to 160-180° C. Water is removed by vacuum during the reaction process. The reaction is monitored by determination of acid value. The acid value will diminish as the reaction proceeds. The reaction is cooled once the acid value fails to change over an additional two hours at temperature. The product is used without purification.

| | Dimer Acid | | Sorbeth Esters 1 | | Sorbeth Ester 2 | |
|---|---|---|---|---|---|---|
| Example | Example | Grams | Example | Grams | Example | Grams |
| 40 | 38 | 535 | 23 | 1076 | 33 | 572 |
| 41 | 38 | 535 | 24 | 2096 | 34 | 1240 |
| 42 | 38 | 535 | 25 | 3390 | 35 | 1684 |
| 43 | 38 | 535 | 26 | 3350 | 36 | 2352 |
| 44 | 38 | 535 | 27 | 4482 | 37 | 3008 |
| 45 | 38 | 535 | 28 | 908 | 23 | 1076 |
| 46 | 38 | 535 | 29 | 1690 | 25 | 3390 |
| 47 | 38 | 535 | 30 | 2282 | 33 | 572 |
| 48 | 38 | 535 | 31 | 2996 | 34 | 1240 |
| 49 | 38 | 535 | 32 | 3260 | 32 | 3260 |
| 50 | 38 | 535 | 33 | 572 | 23 | 1076 |
| 51 | 38 | 535 | 34 | 1240 | 24 | 2096 |
| 52 | 38 | 535 | 35 | 1684 | 25 | 3390 |
| 53 | 38 | 535 | 36 | 2352 | 26 | 3350 |
| 54 | 38 | 535 | 37 | 3008 | 32 | 3260 |

Reaction with Hydrogenated Dimer Acid

A specified number of grams of the specified alkoxylate ester (Examples 23-37) is added to a specified amount of hydrogenated dimer acid (Example 39). The reaction mixture is heated to 160-180° C. Water is removed by vacuum during the reaction process. The reaction is monitored by determination of acid value. The acid value will diminish as the reaction proceeds. The reaction is cooled once the acid value fails to change over an additional two hours at temperature. The product is used without purification.

| | Dimer Acid | | Sorbeth Esters 1 | | Sorbeth Ester 2 | |
|---|---|---|---|---|---|---|
| Example | Example | Grams | Example | Grams | Example | Grams |
| 55 | 39 | 537 | 23 | 1076 | 33 | 572 |
| 56 | 39 | 537 | 24 | 2096 | 34 | 1240 |
| 57 | 39 | 537 | 25 | 3390 | 35 | 1684 |
| 58 | 39 | 537 | 26 | 3350 | 36 | 2352 |
| 59 | 39 | 537 | 27 | 4482 | 37 | 3008 |
| 60 | 39 | 537 | 28 | 908 | 23 | 1076 |
| 61 | 39 | 537 | 29 | 1690 | 25 | 3390 |
| 62 | 39 | 537 | 30 | 2282 | 33 | 572 |
| 63 | 39 | 537 | 31 | 2996 | 34 | 1240 |
| 64 | 39 | 537 | 32 | 3260 | 32 | 3260 |
| 65 | 39 | 537 | 33 | 572 | 23 | 1076 |
| 66 | 39 | 537 | 34 | 1240 | 24 | 2096 |
| 67 | 39 | 537 | 35 | 1684 | 25 | 3390 |
| 68 | 39 | 537 | 36 | 2352 | 26 | 3350 |
| 69 | 39 | 537 | 37 | 3008 | 32 | 3260 |

Applications Examples

Materials and Methods

All Sunscreen formulations were tested for SPF tested using a single port Solar Light Model 15S Xenon Arc. Solar Simulator Lamp. Which has a continuous light spectrum in the UVA and UVB spectrum (290-400 nm). The spectral output of the solar simulator is filtered so that it meets the spectral output requirements for testing Sunscreen Drug Products for over-the-counter human use; Proposed Amendment of Final. Monograph, CFR Part 352,70 (b) Light Sources. Federal Register Vol 72, No. 165, Aug. 27, 2007 and the International Sun Protection Factor (SPF) Test Method, May 2006. perform SPF testing on Formulas 1 and 2 using the same 5 subjects.

To test the SPF increase of sunscreen formulations with the addition of compounds of the present invention were prepared and the sets of formulas were SPF tested on the same subjects. A typical procedure for the preparation of formulas 1-5 is as follows: Disperse A. Add B while heating to 170° F. stir until clear. Add C to A/B while mixing. Cool with stirring to 120° F. and add D. Continue cooling, QS and mix.

| | Formula (% w/w) | | | | |
|---|---|---|---|---|---|
| Ingredient | 1 | 2 | 3 | 4 | 5 |
| Part A | | | | | |
| Water | 74.20 | 67.20 | 69.70 | 62.20 | 57.20 |
| Acrylates/C10-30 Alkyl Acrylate Crosspolymer | 0.25 | 0.25 | 0.25 | 0.25 | 0.25 |
| DiSodium EDTA | 0.05 | 0.05 | 0.05 | 0.05 | 0.05 |
| Part B | | | | | |
| Triethanolamine | 1.00 | 1.00 | 1.00 | 1.00 | 1.00 |
| Part C | | | | | |
| Octocrylene | 3.00 | 3.00 | 3.00 | 3.00 | 3.00 |
| Octisalate | 3.00 | 3.00 | 3.00 | 3.00 | 3.00 |
| Oxybenzone | 2.00 | 2.00 | 2.00 | 2.00 | 2.00 |

-continued

| | Formula (% w/w) | | | | |
|---|---|---|---|---|---|
| Ingredient | 1 | 2 | 3 | 4 | 5 |
| Avobenzone | 1.00 | 1.00 | 1.00 | 1.00 | 1.00 |
| Stearic Acid | 2.00 | 2.00 | 2.00 | 2.00 | 2.00 |
| Glyceryl Monostearate SE | 3.00 | 3.00 | 3.00 | 3.00 | 3.00 |
| Benzyl Alcohol | 1.00 | 1.00 | 1.00 | 1.00 | 1.00 |
| Dimethicone | 0.50 | 0.50 | 0.50 | 0.50 | 0.50 |
| C12-15 Alcohols Benzoate | 8.00 | 8.00 | 8.00 | 8.00 | 8.00 |
| Example 41 | — | 5.00 | 2.50 | 10.00 | 15.00 |
| Octyldodecyl citrate crosspolymer | — | 2.00 | 2.00 | 2.00 | 2.00 |
| Part D | | | | | |
| Parabens/Phenoxyethanol | 1.00 | 1.00 | 1.00 | 1.00 | 1.00 |

| Ingredient | Formula 6 (% w/w) | Formula 7 (% w/w) |
|---|---|---|
| C12-15 Alcohols Benzoate | 30.30 | — |
| Mineral Oil | 30.30 | — |
| Octyl Palmitate | 30.30 | — |
| Spider Ester ESO (sorbeth 2 hexaoleate) | — | 91.00 |
| Octocrylene | 3.00 | 3.00 |
| Octisalate | 3.00 | 3.00 |
| Oxybenzone | 2.00 | 2.00 |
| Avobenzone | 1.00 | 1.00 |

Formulas 1-7 were prepared in the United States by a research consultant and tested in an independent test laboratory. Formulas 8-13 were prepared by SurfaTech Corporation and tested by an independent test laboratory.

Shown in Table 3, SunQuencher Concentrate® was prepared by a series of dilutions of the formula listed in table 4. The results are summarized below.

| Ingredient | % |
|---|---|
| Example 42 | 65.00 |
| Octyldodecyl citrate crosspolymer | 10.00 |
| Octocrylene | 8.33 |
| Octisalate | 8.33 |
| Oxybenzone | 5.55 |
| Avobenzone | 2.80 |

| | Formula | | | | | |
|---|---|---|---|---|---|---|
| Ingredient | 8 | 9 | 10 | 11 | 12 | 13 |
| Example 42 | 0.00 | 7.58 | 22.75 | 0.00 | 13.00 | 39.00 |
| Octyldodecyl citrate crosspolymer | 0.00 | 1.16 | 3.50 | 0.00 | 2.00 | 6.00 |
| Octocrylene | 2.90 | 2.90 | 2.90 | 5.00 | 5.00 | 5.00 |
| Octisalate | 2.90 | 2.90 | 2.90 | 5.00 | 5.00 | 5.00 |
| Oxybenzone | 1.94 | 1.94 | 1.94 | 3.33 | 3.33 | 3.33 |
| Avobenzone | 0.98 | 0.98 | 0.98 | 1.68 | 1.68 | 1.68 |
| C12-15 Alcohols benzoate | 45.66 | 44.26 | 34.97 | 42.50 | 35.00 | 20.00 |
| Caprylic/Capric triglyceride | 45.66 | 44.26 | 34.97 | 42.50 | 35.00 | 20.00 |

The use of compounds of the present invention in the formulation has a dramatic affect upon the SPF of formulations having the same concentration of sunscreen. In other words it makes the sunscreen more effective. Lower levels of sunscreen can be used to obtain the same SPF as formulations using traditional SPF esters The uniformity of the SPF values developed on formulations made and tested by two different labs, one in North America and the other in Europe, is both unexpected and very important. It is well known in the industry that different testing laboratories can obtain significantly different results on the same formula. With this in mind, it is important to note that the SPF results from each separate test 1, 2, and 3 were obtained from the same subjects. For example the same 5 subjects tested by the same clinicians obtained an average SPF of 19 on Formula 1 and an average SPF of 32 on formula 2. Likewise formulas 3, 4, and 5 were tested on the same subjects. Formulas 6 and 7 were tested on the same 3 subject test panel.

The results from formulas 6 and 7 clearly show that on the same subjects the formula consisting entirely of Spider ester ESO as a diluent performed remarkably better than the similar oil made with common oil ingredients Octyl Palmitate, Mineral Oil and C12-15 alcohols Benzoate. Formulas 3, 4, and 5 showed similar results to formula 2, suggesting that in this particular type formulation a broad range of ESO percentages could be used to enhance the SPF. Table 5 shows the results.

| Formula | % Example 41 | SPF | Formula type |
|---|---|---|---|
| 1 | 0.0 | 19 | OW Emulsion |
| 2 | 5.0 | 32 | OW Emulsion |
| 3 | 2.5 | 35.0 | OW Emulsion |
| 4 | 10.0 | 35.0 | OW Emulsion |
| 5 | 15.0 | 30.0 | OW Emulsion |
| 6 | 0.0 | 16.0 | Oil |
| 7 | 91.0 | 29.0 | Oil |
| 8 | 0.0 | 14.8 | Oil |
| 9 | 7.6 | 19.3 | Oil |
| 10 | 22.8 | 30.2 | Oil |
| 11 | 0.0 | 18.1 | Oil |
| 12 | 13.0 | 26.8 | Oil |
| 13 | 39.0 | 58.9 | Oil |

Formulas 6 and 8 are practically identical and the SPF values obtained by the two independent labs was practically identical, SPF 14.8 and 16. Interestingly, formulas 7 and 10 had practically identical SPFs, 29 and 30.2 respectively, but whereas formula 7 had 91% ESO, formula 10 had 22.75%. This suggests that there is an optimum amount of polar solvent needed to increase SPF, and adding additional polar solvent neither helps nor hinders SPF.

| Material | 1A | 1B | 1C | 1D |
|---|---|---|---|---|
| Octylcrylene | 3.00 | 3.00 | 3.00 | 3.00 |
| Octylsalicyate | 3.00 | 3.00 | 3.00 | 3.00 |
| Oxybenzone | 2.00 | 2.00 | 2.00 | 2.00 |
| Avobenzone | 1.00 | 1.00 | 1.00 | 1.00 |
| Example 42 | 0.00 | 9.00 | 18.00 | 27.00 |
| $C_8C_{10}$ Triglycerde | 91.00 | 82.00 | 73.00 | 64.00 |

| Result | 1A | 1B | 1C | 1D |
|---|---|---|---|---|
| SPF | 14.8 | 19.3 | 25.2 | 30.2 |
| Increase of SPF | — | 30.4% | 70.3% | 104.1% |
| UVA/UVB | 1.21 | 1.25 | 1.04 | 0.98 |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains

The invention claimed is:

1. An ester having the following structure:

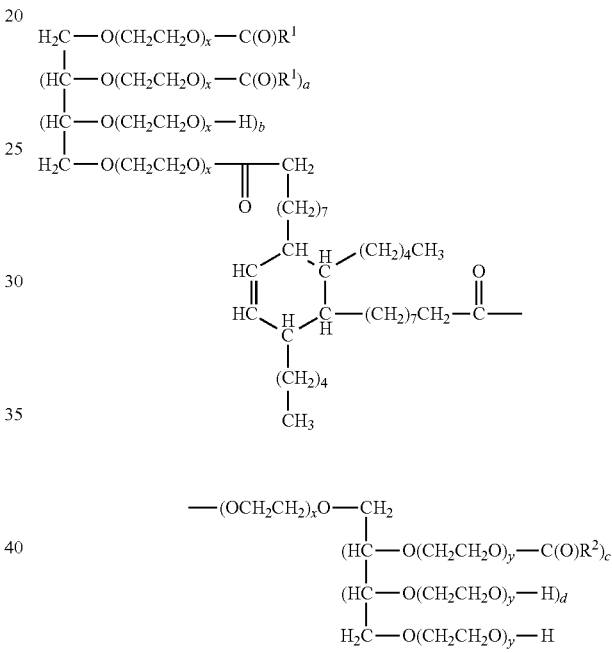

wherein;
   $R^1$ is an alkyl having 7 to 21 carbons atoms;
   $R^2$ is an alkyl having 7 to 21 carbons atoms;
   x is an integer ranging from 1 to 10;
   y is an integer ranging from 1 to 10;
   a is an integer ranging from 0 to 4;
   b is an integer ranging from 0 to 4, with the proviso that a+b equals 4;
   c is an integer ranging from 0 to 4;
   d is an integer ranging from 0 to 4, with the proviso that c+d equals 4.

2. The ester of claim 1 wherein x is 1.

3. The ester of claim 1 wherein x is 3.

4. The ester of claim 1 wherein x is 5.

5. The ester of claim 1 wherein x is 7.

6. The ester of claim 1 wherein x is 10.

7. A process for improving the efficiency of sunscreens, which comprises contacting the skin with an effective protecting concentration of a composition comprising:

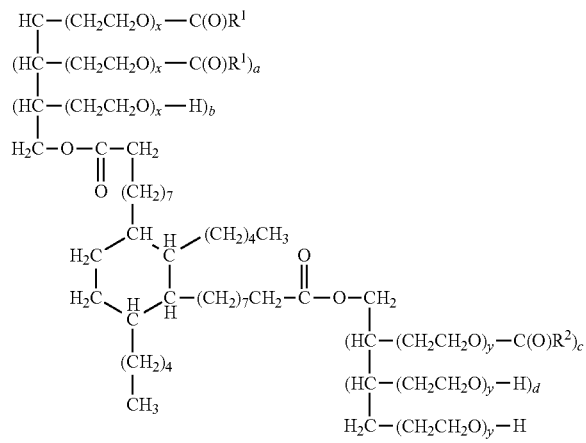

wherein;

$R^1$ is an alkyl having 7 to 21 carbons atoms;

$R^2$ is an alkyl having 7 to 21 carbons atoms;

x is an integer ranging from 0 to 10;

y is an integer ranging from 0 to 10;

a is an integer ranging from 0 to 4;

b is an integer ranging from 0 to 4, with the proviso that a+b equals 4;

c is an integer ranging from 0 to 4;

d is an integer ranging from 0 to 4, with the proviso that c+d equals 4.

and sunscreening actives.

8. The process of claim 7 wherein x is 1.

9. The process of claim 7 wherein x is 3.

10. The process of claim 7 wherein x is 5.

11. The process of claim 7 wherein x is 7.

12. The process of claim 7 wherein x is 10.